United States Patent
Yano et al.

[11] Patent Number: 5,556,636
[45] Date of Patent: Sep. 17, 1996

[54] ADHESIVE COMPOSITION FOR MEDICAL USE

[75] Inventors: Yoshiaki Yano, Kakogawa; Kazuyuki Takeo; Takayoshi Hidaka, both of Kobe, all of Japan

[73] Assignee: Kanegafuchi Kagaku Kogyo Kabushiki Kaisha, Osaka, Japan

[21] Appl. No.: 319,085

[22] Filed: Oct. 6, 1994

Related U.S. Application Data

[60] Continuation of Ser. No. 92,825, Jul. 19, 1993, abandoned, which is a division of Ser. No. 773,262, Oct. 9, 1991, abandoned.

[30] Foreign Application Priority Data

Oct. 22, 1990 [JP] Japan ................................ 2-284745
Oct. 25, 1990 [JP] Japan ................................ 2-289259

[51] Int. Cl.$^6$ ....................................... A61F 13/00
[52] U.S. Cl. ........................ 424/448; 424/447; 424/449
[58] Field of Search ...................... 424/448, 449, 424/447

[56] References Cited

U.S. PATENT DOCUMENTS

| | | | |
|---|---|---|---|
| 4,463,115 | 7/1984 | Hirose et al. | 524/188 |
| 4,655,767 | 4/1987 | Woodard et al. | 424/449 |
| 4,665,127 | 5/1987 | Hirose et al. | 525/100 |
| 4,707,526 | 11/1987 | Sasaki et al. | 525/404 |

FOREIGN PATENT DOCUMENTS 63-68528  3/1988  Japan.

*Primary Examiner*—D. Gabrielle Phelan
*Attorney, Agent, or Firm*—Birch, Stewart, Kolasch & Birch, LLP

[57] ABSTRACT

The present invention is directed to a sticky composition for medical use comprising a tackifier resin and an oxyalkylene polymer having a silicon-containing group which can be crosslinked by forming a siloxane bond, wherein silicon atom thereof is bound with a hydroxyl group or hydrolytic group, and to a transdermal drug delivery preparation incorporating said sticky composition as a drug carrier. The sticky composition of the present invention possesses excellent adhesive properties, very low skin irritancy and good compatibility with the site of plastering and thus perform as a very safe and effective medical adhesive. The transdermal drug delivery preparation of the present invention offers excellent drug release from the sticky composition.

10 Claims, 2 Drawing Sheets

ADHESIVE COMPOSITION FOR MEDICAL USE

This application is a continuation of application Ser. No. 08/092,825 filed on Jul. 19, 1993, now abandoned, which is a divisional application of Ser. No. 07/773,262 filed on Oct. 9, 1991, now abandoned.

FIELD OF THE INVENTION

The present invention relates to a sticky composition for medical use and a transdermal drug delivery preparation incorporating it, more specifically to a sticky composition for medical use which causes little skin irritation and is hence safe and which has excellent adhesive properties and a transdermal drug delivery preparation for treating a diseased part of body or for delivering a drug to the circulatory system.

BACKGROUND OF THE INVENTION

Traditionally, plasters applied to the body to treat skin lesions or to transdermally deliver drugs to internal lesions or the circulatory system and other organs and other medical adhesives used in medical devices are prepared from polyvinyl alkyl ethers, poly(metha)acrylates, 2-ethylhexyl acrylate-2-ethylhexyl methacrylate copolymers, 2-ethylhexyl acrylate-vinylpyrrolidone copolymers, polyurethane, styrene-isoprene-styrene block copolymers, polyisobutylene rubber, polyisoprene rubber, butyl rubber, natural rubber, silicone resin and other substances. To give a pressure-sensitive adhesion property to these copolymers, known tackifiers, softening agents, fillers, anti-aging agents and other additives are added.

These sticky compositions are required to be safe with little skin irritation and to have well-balanced adhesive properties (tack, adhesion, cohesion). However, none of them meets all these requirements. For example, sticky compositions based on acrylic resin are known to have skin irritancy causing skin sweating, flare or edema. Sticky compositions based on silicone resin are faulty in that the plaster is liable to detaching due to sweating or the plaster becomes more likely to be detached when it is attached to the joint.

In recent years, there have been remarkable progress based on the concept of drug delivery system in the development of transdermal drug delivery preparations aiming at systemic action as well as action on skin lesions. These preparations have been increasingly recognized to be useful as sustained-release preparations. This kind of conventional transdermal drug delivery preparations includes those using a medical adhesive as an adhesive base comprising an adhesive polymer layer as described above which contains a drug and a release aid which promotes the release of the drug on a drug-impermeable backing material. By plastering them on the body, drugs are delivered to diseased parts of the body or to the circulatory system.

The adhesive base for the transdermal drug delivery preparation is required to have high safety and well-balanced adhesive properties and offer good drug release. Particularly in transdermal drug delivery preparations aiming at systemic action, drug release from drug carrier is known to be a key factor. Although the silicone elastomer described above is widely used as a base for implantation preparations and transdermal drug delivery devices and as a drug carrier for various other preparations because it is very safe, it is known to have a problem in drug release in addition to the above-mentioned problems such as the tendency for plaster to be detached due to sweating when it is used as an adhesive base for transdermal drug delivery preparations. In transdermal drug delivery preparations incorporating a silicone elastomer as an adhesive polymer layer, i.e., an adhesive base, the releasing property for the drug retained by the silicone elastomer, i.e., an active ingredient pharmaceutical compound, is very high, provided that the drug has an extremely high vapor pressure like nitroglycerin; and very useful products of devices have been developed. However, the drug releasing property of silicone elastomer is usually very low; therefore, development of devices incorporating the silicone elastomer described above is limited to drugs whose effective dose is low like scopolamine.

SUMMARY OF THE INVENTION

It is an object of the present invention to provide a sticky composition for medical use which causes very little skin irritation and which has excellent adhesive properties and good compatibility with the site of plastering.

It is another object of the invention to provide a transdermal drug delivery preparation which is very safe and which offers good drug release.

To solve the problems described above, the present inventor made investigations. As a result, the inventor found that a sticky composition comprising a tackifier and an oxyalkylene polymer having a silicon-containing group which can be crosslinked by forming a siloxane bond, wherein silicon atom thereof is bound with a hydroxyl group or hydrolytic group, can serve as a medical adhesive having excellent safety and adhesive properties, and developed the invention. Accordingly, the present invention is based on the finding that the sticky composition for medical use of the present invention causes very little skin irritation and has excellent adhesive properties.

The inventor made further investigations to overcome the drawbacks of conventional transdermal drug delivery preparations and developed the transdermal drug delivery preparation of the present invention, which comprises a mixture of a transdermally absorbable pharmaceutical compound as an active ingredient and an auxiliary agent in an elastomer of the sticky composition described above as a base which offers good release of the active ingredient drug.

Accordingly, the present invention comprises the following:

(1) A sticky composition for medical use comprising a tackifier resin and an oxyalkylene polymer having a silicon-containing group which can be crosslinked by forming a siloxane bond, wherein silicon atom thereof is bound with a hydroxyl group or hydrolytic group.

Examples of the silicon-containing group include those represented by the formula II:

wherein X represents an hydroxyl group or hydrolytic group; when there are two or more X groups, they may be identical or not; $R^2$ represents a monovalent hydrocarbon group having 1 to 20 carbon atoms or a triorganosiloxy group represented by $(R')_3SiO$— (R' represents a monovalent hydrocarbon group having 1 to 20 carbon atoms; the three R' groups may be identical or not; when there are two or more $R^2$ groups, they may be identical or not,; a represents 0, 1, 2 or 3; b represents 0, 1 or 2; $1\leq a+mb$, wherein m represents 0 or an integer of 1 to 19, and when m is 2 or more, the b numbers may not be identical.

(2) A transdermal drug delivery preparation incorporating as a drug carrier a sticky composition comprising a tackifier resin and an oxyalkylene polymer having a silicon-containing group which can be crosslinked by forming a siloxane bond, wherein silicon atom thereof is bound with a hydroxyl group or hydrolytic group.

Examples of the silicon-containing group used here include those represented by Formula II as in (1) above.

DETAILED DESCRIPTION OF THE INVENTION

Figure 1:
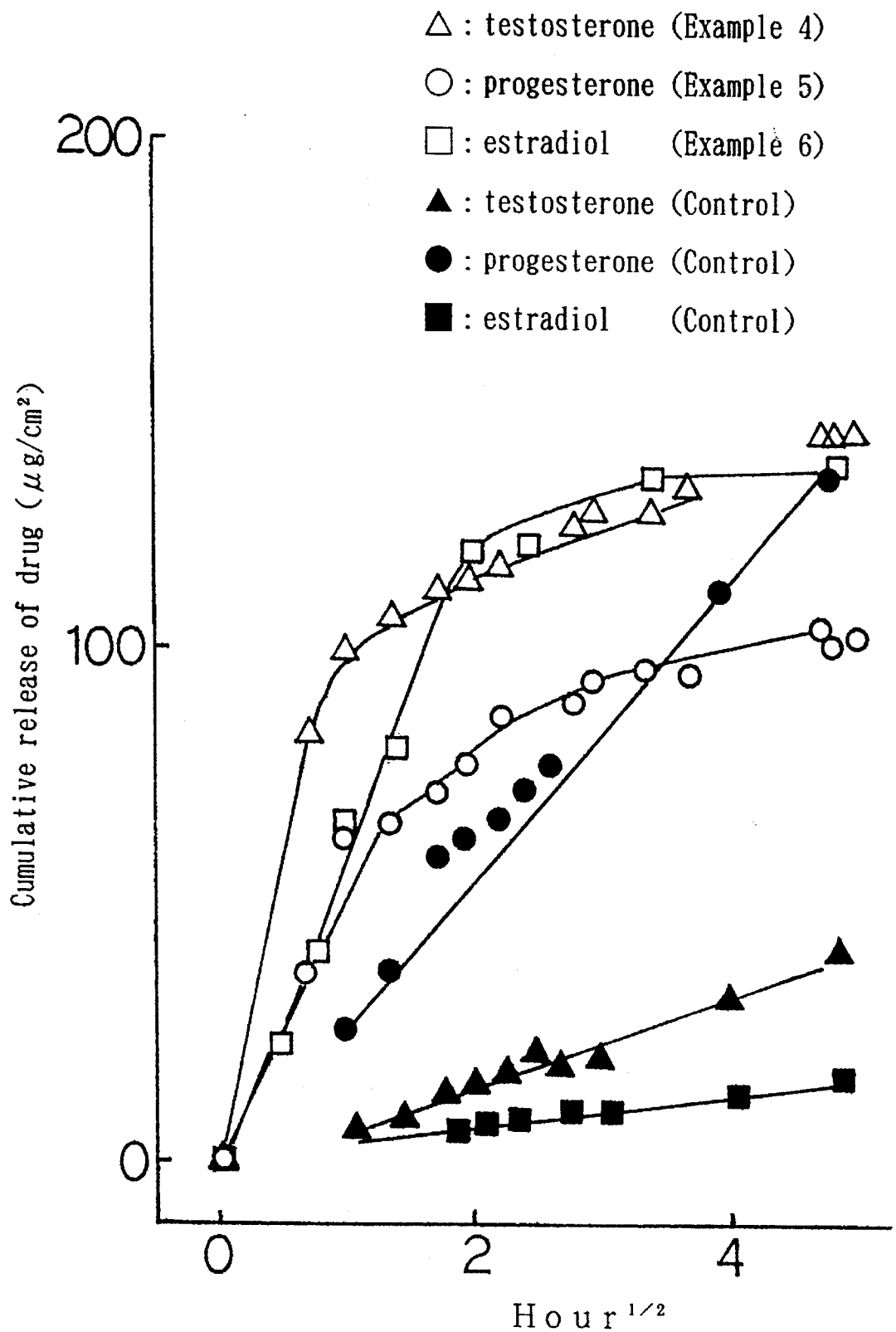
FIG. 1 shows the drug releases in diffusion cell from the preparations obtained in Examples 4 through 6 and a control preparation.

As an oxyalkylene polymer having a silicon-containing group in the molecular structure for the present invention, known polymers disclosed in Japanese Patent Examined Publication Nos. 36319/1970, 12154/1971 and 32673/1974, Japanese Patent Laid-Open Nos. 156599/1975, 73561/1976, 6096/1979, 82123/1980, 123620/1980, 125121/1980, 131022/1980, 135135/1980 and 137129/1980 and other publications can be used with no limitation.

The molecular chain of the oxyalkylene polymer preferably has a repeat unit essentially represented by the formula I:

$$—R^1—O—\quad (I)$$

wherein $R^1$ represents a divalent organic group, with most preference given to the case where the majority of $R^1$ is a hydrocarbon group having 3 or 4 carbon atoms. Examples of $R^1$ include the following:

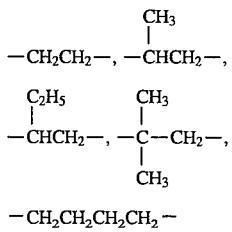

$$—CH_2CH_2CH_2CH_2—$$

The following compound is most preferable from the viewpoint of adhesive properties.

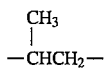

The molecular chain of oxyalkylene polymer described above may comprise only one kind of repeat unit or two or more kinds of repeat unit.

The repeat unit represented by the formula $—R^1—O—$ is contained in the polymer at normally over 50% (% by weight, the same applies below), preferably over 70%, and still more preferably over 80%.

The silicon-containing group for the present invention is a well known functional group. Typical examples thereof include the group represented by the formula II:

wherein X represents an hydroxyl group or hydrolytic group; when there are two or more X groups, they may be identical or not; $R^2$ represents a monovalent hydrocarbon group having 1 to 20 carbon atoms or a triorganosiloxy group represented by $(R')_3SiO—$ (R' represents a monovalent hydrocarbon group having 1 to 20 carbon atoms; the three R' groups may be identical or not); when there are two or more $R^2$ groups, they may be identical or not; a represents 0, 1, 2 or 3; b represents 0, 1 or 2; $1\leq a+mb$, wherein m represents 0 or an integer of 1 to 19, and when m is 2 or more, the b numbers may not be identical.

From the economic and other viewpoints, the silicon-containing group described above is preferably a group wherein m is 0 and which is represented by the formula III:

wherein $R^2$ has the same definition as above; n represents 1, 2 or 3.

Examples of the hydrolytic group in Formula II include a halogen atom, hydrogen atom, alkoxy group, acyloxy group, ketoximate group, amino group, amide group, aminooxy group, mercapto group and alkenyloxy group, with preference given to an alkoxy group such as a methoxy group or ethoxy group, since they are mildly hydrolytic.

Examples of the hydrocarbon group having 1 to 20 carbon atoms for $R^2$ in Formula II and of the monovalent hydrocarbon group having 1 to 20 carbon atoms for R' in $(R')_3SiO—$ include alkyl groups such as methyl group and ethyl group, cycloalkyl groups such as cyclohexyl group, aryl groups such as phenyl group and aralkyl groups such as benzyl group, with preference given to methyl group from the viewpoint of reactivity.

For sufficient hardening set, the number of silicon-containing groups in the oxyalkylene polymer is normally not less than 1, preferably not less than 1.1, and still more preferably not less than 1.5 on average.

Although the silicon-containing group may be located on a side chain of the molecular chain of the oxyalkylene polymer, it is preferably present in a terminal. The number-average molecular weight of the oxyalkylene polymer is normally 500 to 30000, preferably 3000 to 15000, and still more preferably 5000 to 10000.

The oxyalkylene polymer may be used singly or in combination of two or more kinds.

The oxyalkylene polymer for the present invention may be one of the known ones proposed in various publications as stated above. Therefore, these oxyalkylene polymers can easily be prepared by known methods disclosed in these known publications. Examples thereof include MS Polymer 20A (functional group: $—SiCH_3(OCH_3)_2$, number-average molecular weight: 7500), MS Polymer #300 (functional group: $—SiCH_3(OCH_3)_2$, number-average molecular weight: 8500), SILYL 5A01 (functional group: $—SiCH_3(OCH_3)_2$, number-average molecular weight: 8500), SILYL 5B25 (functional group: $—SiCH_3(OCH_3)_2$, $—NH_2$, number-average molecular weight: 8000), BILYL 5B30 (functional group: $—SiCH_3(OCH_3)_2$, $—NH_2$, number-average molecular weight: 5000), produced by Kanegafuchi Chemical Industry Co., Ltd..

The sticky composition of the present invention contains normally 10 to 140 parts by weight of a compatible tackifier resin and 1 to 30 parts by weight of a setting catalyst, relative to 100 parts by weight of the oxyalkylene polymer. The amounts of tackifier resin below 10 parts by weight or above 140 parts by weight are undesirable because the adhesion is insufficient in the former case and no desired effect is obtained in proportion to the amount added and paste retention can occur on the subject of plastering in the latter case.

The tackifier resin is not subject to limitation, as long as it is compatible with the oxyalkylene polymer for the present invention. Known tackifier resins can be used, such as rosin resins (rosin, rosin ester, hydrogenated rosin), phenol resins, terpene phenol resins, xylene resins, aliphatic petroleum resins, aromatic petroleum resins, terpene resins and cumarone resins, with preference given to rosin ester resins and terpene phenol resins.

As setting catalysts, known tin or aluminum based catalysts, amines such as dibutylamine-2-ethylhexoate and other acidic or alkaline catalysts can be used, with preference given to aluminum based catalysts such as aluminum chelate and aluminum alcoholate. As anti-aging agents, known substances such as BHT (benzenehydroxytoluene) and vitamin E can be used. Also, these sticky compositions may be formulated with other known bases etc. for various purposes.

The sticky composition for medical use of the present invention can be prepared by dissolving an oxyalkylene polymer, tackifier resin, setting catalyst, anti-aging agent and other additives as described above in a solvent such as isopropyl alcohol, ethanol, methanol, acetone, toluene or ethyl acetate. The preparation thus obtained can be used as a sticky composition after the process of coating, forming and setting, for instance.

Although the solvent is not subject to limitation, it is preferable to use ethanol, isopropyl alcohol or the like from the viewpoint of safety. The sticky composition thus obtained can be used for medical use in plaster, adhesive sheet and other forms by conventional methods. Particularly, the sticky composition can be used as a drug carrier in the transdermal drug delivery preparation of the present invention.

The skin irritancy of the sticky composition for medical use of the present invention is very low. To confirm this, the oxyalkylene polymer itself was tested for irritancy. It was found non-irritative, whose PCI (primary cutaneous irritation index) was 0 as determined by a primary skin irritation test in rabbits (Draize's method, 1959, FDA). Even when the tackifier resin, setting catalyst, anti-aging agent and other bases described above were added to the oxyalkylene polymer to yield a sticky composition, the PCI of the sticky composition was close to about 1. Since the PCI classification comprises three grades of "weak irritant" for scores 0 to 2, "moderate irritant" for 3 to 5 and "strong irritant" for 6 to 8, the sticky composition for medical use of the present invention can be judged to have very low skin irritancy.

With respect to properties other than the skin irritancy, sticky compositions for medical use are usually required to have sufficient vapor permeability and oxygen permeability, moderate flexibility, good stability to heat and light and well-balanced adhesive properties without involving deterioration of the sticky composition or adhesion failure between the sticky composition layer and the backing material.

Since the sticky composition for medical use of the present invention meets all these requirements for properties and has sufficient vapor permeability, the plaster does not become detached from skin due to sweating.

The transdermal drug delivery preparation of the present invention is characterized by the use of the sticky composition for medical use of the present invention described above as a drug carrier. The drug for the present invention, i.e., a pharmaceutical compound as an active ingredient, is not subject to limitation, as long as it is transdermally absorbable. Examples of such compounds include the following:

a) Antibiotics such as penicillins, cephalosporins, erythromycins, tetracyclines, macrolides, aminoglycosides, fosfomycins and rifampicins.

b) Antipyretics, analgesics and anti-inflammatory drugs such as mefenamic acid, flufenamic acid, indometacin, diclofenac, acetaminophen, alclofenac, oxyphenbutazone, phenylbutazone, ibuprofen, ketoprofen, salicylic acid, methyl salicylate, L-menthol, camphor, sulindac, naproxen, fenbufen, aspirin, sulpyrine, tiaramide hydrochloride and piroxicam.

c) Antihistaminics such as $\alpha$-chlorpheniramine maleate, diphenylpyraline, diphenhydramine, clemastine fumarate and promethazine hydrochloride.

d) Psychotropic drugs for hypnosis, sedation and ataraxia such as diazepam, chlorpromazine hydrochloride, chlordiazepoxide, sulpiride, haloperidol, ethyl loflazepate, fluphenazine, thioridazine, fludiazepam, flunitrazepam, phenobarbital, amobarbital, cyclobarbital, triazolam and nitrazepam.

e) Coronary vasodilators such as nitroglycerin, isosorbide dinitrate, nitroglycol, erythritol tetranitrate, pentaerythritol tetranitrate, verapamyl (hydrochloride), nifedipine, dipyridamole and diltiazem hydrochloride.

f) Antiarrhythmics and antihypertensive drugs such as propranolol (hydrochloride), pindolol, clonidine (hydrochloride), bupranolol, indenolol, nilvadipine, nipradilol, bucumolol, hydrazinc hydrochloride and rescinnamine.

g) Hypotensive diuretics such as hydrothiazide, benzylhydrochlorothiazide and cyclopenthiazide and diuretics such as furosemide, mefruside, trichlormethiazide and thiobromine.

h) Chemotherapeutic drugs such as aciclovir, nalidixic acid and sulfa drugs.

i) Anticancer agents such as 5-FU, vincristine, adriamycin, bleomycin, mitomycin, cisplatin and therarubicin.

j) Antiemetics agents such as metoclopramide, clebopride, scopolamine (hydrobromide) and domperidone.

k) Vitamins such as vitamin A, vitamin E, vitamin K, ergocalciferol, cholecalciferol, octotiamine and riboflavin tetrabutyrate.

l) Antispasmodics such as nitrazepam, clonazepam, baclofen and meprobamate.

m) Antitussives such as dextromethorphane, terbutaline (sulfate), ephedrine (hydrochloride), salbutamol (hemisulfate), isoproterenol and trimetoquinol hydrochloride.

n) Cardiacs such as prenylamine lactate, digitoxin and digoxin.

o) Anesthetics such as lidocaine, benzocaine and ethyl-p-aminobenzoate.

p) Cerebrovascular improvers such as Hydergine, ergot alkaloid and ifenprodil.

q) Antifungal drugs such as pentamycin, amphotericin B, pyrrolnitrin, clotrimazole, benzalkonium chloride, nitrofurazone, nystatin and acetosulfamine.

r) Steroids such as hydrocortisone, prednisolone, paramethasone, beclomethasone dipropionate, flumethasone, betamethasone, betamethasone valerate, dexamethasone, triamcinolone, triamcinolone acetonide, fluocinolone, fluocinolone acetonide, clobetasol propionate, progesterone, testosterone and estradiol.

s) Anti-parkinsonism drugs such as L-dopa, bromocriptine mesilate, trihexyphenidyl hydrochloride, mazaticol hydrochloride and biperiden hydrochloride.

t) Biologics such as TRH, LHRH, TNF, lymphotoxin, interferon, urokinase, insulin, calcitonin, their derivative polypeptides and prostaglandins.

u) Others such as tolbutamide and other antidiabetic drugs, colchicine and other anti-gout drugs and nicotine and other smoking suppressors.

These drugs may be used in combination of two or more kinds as necessary.

The transdermal drug delivery preparation of the present invention can be prepared as follows. A drug, i.e., a pharmaceutical compound as an active ingredient, is normally uniformly mixed in alcohol along with an auxiliary agent to yield a pasty or dissolved mixture. The auxiliary agent is used as necessary. Examples thereof include plasticizers such as liquid silicone, absorption promoters such as isopropyl myristate, azone, urea, glycerol, monoglyceride and diisopropyl adipate and fillers such as silica, potassium carbonate, kaolin and talc.

Examples of alcohols which are normally used as solvents include isopropyl alcohol, methanol, ethanol and butanol, with preference given to isopropyl alcohol and ethanol from the viewpoint of safety.

The resulting dissolved or pasty mixture is uniformly mixed in the sticky composition described above to dissolve or disperse as fine powder. When the sticky composition has been formulated with a setting catalyst, it is placed in an appropriate mold and set and formed at room temperature or increased temperature to yield the transdermal drug delivery preparation of the present invention. When the sticky composition has not been formulated with a setting catalyst, a setting catalyst is appropriately added to the mixture and thoroughly mixed quickly, after which the mixture is placed in an appropriate mold and set and formed at room temperature or increased temperature to yield the transdermal drug delivery preparation of the present invention.

The transdermal drug delivery preparation of the present invention is preferably prepared to a composition of 0.05 to 40 parts by weight of pharmaceutical compound, 1 to 30 parts by weight of auxiliary agent and 30 to 90 parts by weight of sticky composition, though the content of the pharmaceutical compound in the finished preparation varies depending on the kind of the drug used, i.e., the pharmaceutical compound as an active ingredient and the kind of target disease.

The transdermal drug delivery preparation thus obtained comprises the sticky composition of the present invention described above as a drug carrier and offers excellent drug release.

Various experimental models for drug release are known. For example, in drug release experiments using a diffusion cell, the transdermal drug delivery preparation of the present invention offers quicker and more release in comparison with conventional preparations incorporating a silicone elastomer.

The transdermal drug delivery preparation of the present invention is used in accordance with ordinary methods, though dosage, administration frequency and other factors vary depending on the kind of the drug used, i.e., the pharmaceutical compound as an active ingredient and the kind of target disease.

As stated above, the sticky composition for medical use of the present invention possesses excellent adhesive properties, very low skin irritancy and good compatibility with the site of plastering and thus perform as a very safe and effective medical adhesive. This sticky composition for medical use can be used for artificial anus, medical tapes, prevention of bedsores, attaching medical devices or their terminals to the human body and other purposes as well as for percutaneous and permucosal administration.

Incorporating an oxyalkylene polymer, the transdermal drug delivery preparation of the present invention offers excellent drug release from the sticky composition of the invention, which is a drug carrier. Therefore, the transdermal drug delivery preparation of the present invention allows absorption of a sufficient amount of drug via skin, which is thus easy to apply and permits a high level of drug concentration in blood.

EXAMPLES

The present invention is hereinafter described in more detail by means of the following working examples and test examples, but the invention is not limited by these examples and affords various applications, as long as they are not deviated from the technical scope of the invention.

Preparation of oxyalkylene polymer

The oxyalkylene polymer for the present invention, having a silicon-containing group which can be crosslinked by forming a siloxane bond, wherein silicon atom thereof is bound with a hydroxyl group or hydrolytic group, can be prepared as follows. First, 320 g of a polyoxypropylene glycol having an average molecular weight of 3200 (of the total terminal group content, allyl ether groups account for 15%, propenyl ether groups account for 3% and hydroxyl groups account for 82%) was taken in a nitrogen-substituted 1-liter pressure-resistant reactor equipped with a stirring rod. Subsequently, 40.8 g of powdered caustic soda (purity 98%) was added, and the temperature was raised to 60 ° C. Then, 7.76 g of bromochloromethane was added, followed by 10 hours of reaction at 60° C. Subsequently, the temperature in the reaction part was reduced to 50 ° C., and 9.2 g of allyl chloride was added, followed by 10 hours of reaction at 50 ° C. After completion of the reaction, the reaction product was transferred to a beaker, diluted with 1000 g of normal hexane and then treated with 50 g of aluminum silicate at normal temperature for 1 hour while stirring. After filtration, the resulting cake was washed with normal hexane several times. The volatile substances were evaporated off from the filtrate to yield 300 g of a propylene oxide polymer having an average molecular weight of 8000. The terminal groups of the polymer were 90% of allyl ether groups, 8% of propenyl ether groups and 2% of hydroxyl groups. 84 g of the polymer obtained on a 500-ml pressure-resistant reactor equipped with a stirring rod was taken. 0.05 ml of catalyst solution of chloroplatinic acid (2 g of $H_2PtCl_6.6H_2O$ was dissolved in 20 ml of isopropanol and 78 ml of tetrahydrofuran) and 2.1 g of methyl dimethoxysilane were added, followed by 8 hours of reaction at 100° C. Then, the volatile substances were evaporated off to yield an alkylene oxide polymer wherein the group represented by the following formula accounts for 82% of the terminal groups.

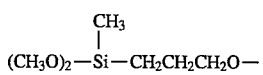

Example 1

To 100 parts by weight of an oxyalkylene polymer (SILYL 5A01, produced by Kanegafuchi Chemical Industry Co., Ltd.), which has a molecular weight of 8500 and a terminal silicon-containing group represented by —SiCH$_3$(OCH$_3$)$_2$, 80 parts by weight of rosin ester (ester gum AAG, produced by Arakawa Kagaku) as a tackifier resin, 10 parts by weight of a setting catalyst (aluminum chelate ALCH, produced by Kawaken Fine Chemical) and 0.5 part by weight of an anti-aging agent BHT were added, and a sticky composition polymer was prepared using isopropyl alcohol. The sticky composition polymer was coated and dried on a polyethylene film of 80 μm in thickness subjected to corona discharge treatment on one face to a dry film thickness of 50 μm to yield an adhesive plaster.

Example 2

To 100 parts by weight of an oxyalkylene polymer (SILYL 5A01, produced by Kanegafuchi Chemical Industry Co., Ltd.), which has a molecular weight of 8500 and a terminal silicon-containing group represented by —SiCH$_3$(OCH$_3$)$_2$, 40 parts by weight of terpene phenol resin (YS Polyster S145, produced by Yasuhara Chemical) as a tackifier resin, 10 parts by weight of a setting catalyst (aluminum chelate ALCH, produced by Kawaken Fine Chemical) and 0.5 part by weight of an anti-aging agent BHT were added, and a sticky composition polymer was prepared using isopropyl alcohol. The sticky composition polymer was coated and dried on a polyethylene film of 80 μm in thickness subjected to corona discharge treatment on one face to a dry film thickness of 50 μm to yield an adhesive plaster.

Example 3

To 100 parts by weight of an oxyalkylene polymer (MS polymer 20A, produced by Kanegafuchi Chemical Industry Co., Ltd.), which has a molecular weight of 7500 and a terminal silicon-containing group represented by —SiCH$_3$(OCH$_3$)$_2$, 80 parts by weight of rosin ester (ester gum AAG, produced by Arakawa Kagaku) as a tackifier resin, 10 parts by weight of a setting catalyst (aluminum chelate ALCH, produced by Kawaken Fine Chemical) and 0.5 part by weight of an anti-aging agent BHT were added, and a sticky composition polymer was prepared using isopropyl alcohol. The sticky composition polymer was coated and dried on a polyethylene film of 80μm in thickness subjected to corona discharge treatment on one face to a dry film thickness of 50 μm to yield an adhesive plaster.

Example 4

To the sticky composition polymer prepared in Example 1, testosterone as a drug was added to a concentration of 2.5 wt. %, followed by setting and forming to yield the transdermal drug delivery preparation of the present invention.

Example 5

To the sticky composition polymer prepared in Example 1, progesterone as a drug was added to a concentration of 2.5 wt. %, followed by setting and forming to yield the transdermal drug delivery preparation of the present invention.

Example 6

To the sticky composition polymer prepared in Example 1, estradiol as a drug was added to a concentration of 2.5 wt. %, followed by setting and forming to yield the transdermal drug delivery preparation of the present invention.

Example 7

To the sticky composition polymer prepared in Example 3, testosterone as a drug was added to a concentration of 2.5 wt. %, followed by setting and forming to yield the transdermal drug delivery preparation of the present invention.

Example 8

To the sticky composition polymer prepared in Example 3, progesterone as a drug was added to a concentration of 2.5 wt. %, followed by setting and forming to yield the transdermal drug delivery preparation of the present invention.

Example 9

To the sticky composition polymer prepared in Example 3, estradiol as a drug was added to a concentration of 2.5 wt. %, followed by setting and forming to yield the transdermal drug delivery preparation of the present invention.

Test Example 1

Test for changes in appearance and adhesive properties

With respect to the adhesive plasters prepared in Examples 1, 2 and 3, appearance, finger stickiness and tack value were examined immediately after preparation, after storage at room temperature for 60 days and after storage in aluminum foil package at 40° C. for 60 days.

For changes in appearance, the sample had a totally milky white, uniform adhesive layer immediately after preparation, which appearance remained unchanged even after 60 days of storage at room temperature and after 60 days of storage in aluminum foil package at 40° C.

As for finger stickiness, good results were obtained immediately after preparation and after storage.

Tack value (J. Dow's method, JIS Z 0237) was about 20 immediately after preparation, which remained unchanged even after storage. Good adhesive properties were noted.

Test Example 2

Practical application test for plastering to the human body

With respect to the adhesive plasters prepared in Examples 1, 2 and 3, 1 cm×1 cm test pieces cut from the adhesive plasters immediately after preparation and after 60 days of storage at room temperature, respectively, were simultaneously plastered to the upper arm in 10 subjects, and changes in the adhesion condition was monitored for 24 hours.

Good results were obtained in all 10 subjects; none of the test pieces became detached after 24 hours. Skin compatibility during plastering was good.

Test Example 3

Primary skin irritation test

With respect to the adhesive plasters prepared in Examples 1, 2 and 3, 2.5 cm×2.5 cm test pieces cut from the adhesive plasters immediately after preparation and after 60 days of storage at room temperature, respectively, were simultaneously plastered to the upper arm in 10 subjects, and the plasters were removed after 24 hours. Within 30 to 60 minutes after removal, the plastering site was visually examined for the degree of erythema. Nothing more than very slight erythema was observed.

Test Example 4

Evaluation of drug release

Drug release from each of the testosterone, progesterone and estradiol preparations obtained in Examples 4 through 9 was compared with drug release from each of testosterone, progesterone and estradiol preparations prepared using a silicone elastomer.

The silicone elastomer used was a product of Dow Corning (Dow Corning® 2920 Medical Adhesive), to which testosterone, progesterone or estradiol was added to reach a concentration of 2.5 wt. %, followed by setting and forming. For this test, each sample was made to have a film thickness of 50 μm. After loading on a vertical diffusion cell produced by Crown-Glas Company, each sample was tested for drug release in a saline containing 40% polyethylene glycol 400 as a elution solvent.

Cumulative release of testosterone, progesterone or estradiol was determined by HPLC on a time basis. HPLC determinations were made using a Cosmosil 5 CN-R column (4.6 mm×150 mm) at a flow rate of 1.0 ml/min in a $CH_3CH/H_2O$ (40/60) solvent system for testosterone, progesterone or estradiol.

The results are shown in FIG. 1. From FIG. 1, it is evident that drug release from the preparations obtained in Examples 4 though 6 was better than that from the control preparation incorporating a silicone elastomer. The same tendency was noted in the preparations obtained in Examples 7 through 9 (data is not given in FIG. 1). In the transdermal drug delivery preparation of the present invention, drug release from the sticky composition as a drug carrier is extremely higher than that obtained by using the control silicone elastomer.

Test Example 5

Determination of drug concentration in blood

Male rats at 7 weeks of age with their hair clipped using electric clippers were subjected to plastering of the estradiol preparation of Example 6 or 9 or a control estradiol preparation incorporating the same silicone elastomer as used in Test Example 4 in the form of a 5 $cm^2$ piece (n=3). At 2, 8 and 24 hours following plastering, blood was collected and serum was separated. The serum samples thus obtained were subjected to radioimmunoassay to determine the estradiol concentration.

Figure 2:
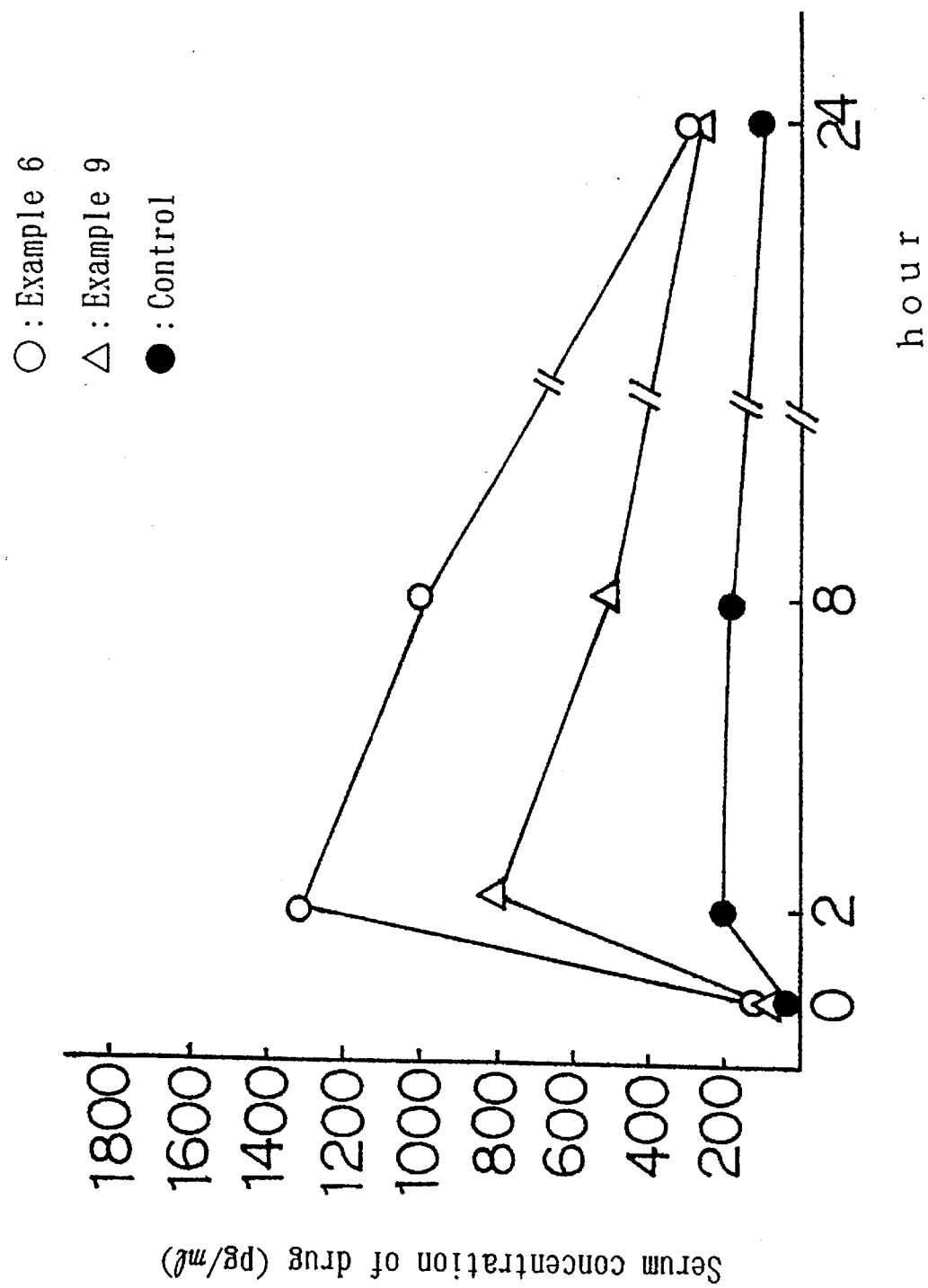
FIG. 2 shows the time courses of drug concentration in rat blood for the preparations obtained in Examples 6 and 9 and a control preparation.

The results are shown in FIG. 2. The estradiol preparations according to the present invention yielded good drug concentrations in blood and offered good sustained release. On the other hand, the rats to which the control estradiol preparation was plastered had very low drug concentrations in blood.

What is claimed is:

1. A transdermal drug delivery preparation comprising at least one transdermally absorbable pharmaceutical compound selected from the group consisting of testosterone, progesterone and estradiol of which an amount of not less than 39% is released within one hour after application, and an adhesive composition as a drug carrier, said adhesive composition comprising a tackifier resin and an oxyalkylene polymer having at least one silicon-containing group, which can be crosslinked through a siloxane of said group, wherein said silicon-containing group is represented by the formula II:

wherein X represents an hydroxyl group or hydrolytic group and when there are two or more X groups, the X groups may be the same or different; $R^2$ represents a monovalent hydrocarbon group having 1 to 20 carbon atoms or a triorganosiloxy group represented by $(R')_3SiO-$, wherein R' represents a monovalent hydrocarbon group having 1 to 20 carbon atoms and the three R' groups may be the same or different, and when there are two or more $R^2$ groups, the $R^2$ groups may be the same or different; a represents 0, 1, 2 or 3; b represents 0, 1 or 2; $1 \leq a+mb$, wherein m represents 0 or an integer of 1 to 19, and when m is 2 or more, the b numbers may not be identical.

2. A transdermal drug delivery preparation according to claim 1, wherein said hydrolyric group represented by X is selected from the group consisting of a halogen atom, a hydrogen atom, an alkoxy group, an acyloxy group, a ketoximate group, an amino group, an amide group, an aminooxy group, a mercapto group and an alkenyloxy group.

3. A transdermal drug delivery preparation according to claim 2, wherein said alkoxy group is a methoxy group or ethoxy group.

4. A transdermal drug delivery preparation according to claim 1, wherein said monovalent hydrocarbon represented by $R^2$ is selected from the group consisting of an alkyl group, a cycloalkyl group, an aryl group and an aralkyl group.

5. A transdermal drug delivery preparation according to claim 4, wherein said monovalent hydrocarbon is a methyl group.

6. A transdermal drug delivery preparation according to claim 1, wherein the number of said silicon-containing group in the oxyalkylene polymer is not less than 1.

7. A transdermal drug delivery preparation according to claim 1, wherein the number-average molecular weight of said oxyalkylene polymer is 500 to 30000.

8. A transdermal drug delivery preparation according to claim 1, wherein said oxyalkytene polymer has a group represented by the following formula at the terminal end thereof

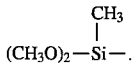

9. A method of treating human skin with a transdermal drug delivery preparation from which an amount of not less than 39% of a drug selected from the group consisting of testosterone, progesterone and estradiol is released within one hour after application, comprising applying the drug in an adhesive composition comprising a tackifier resin and an oxyalkylene polymer having at least one silicon-containing group, which can be crosslinked through a siloxane of said group, wherein said silicon-containing group is represented by the formula II:

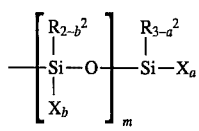 (II)

wherein X represents an hydroxyl group or hydrolyric group and when there are two or more X groups, the X groups may be the same or different; $R^2$ represents a monovalent hydrocarbon group having 1 to 20 carbon atoms or a triorganosiloxy group represented by $(R')_3SiO—$, wherein R' represents a monovalent hydrocarbon group having 1 to 20 carbon atoms and the three R' groups may be the same or different, and when there are two or more $R^2$ groups, the $R^2$ groups may be the same or different; a represents 0, 1, 2 or 3; b represents 0, 1 or 2; $1 \leq a+mb$, wherein m represents 0 or an integer of 1 to 19, and when m is 2 or more, the b numbers may not be identical, to the human skin.

10. A method of releasing a drug in a high initial releasing ratio with a transdermal drug delivery preparation from which an amount of not less than 39% of a drug selected from the group consisting of testosterone, progesterone and estradiol is released within one hour after application, comprising applying the drug in an adhesive composition comprising a tackifier resin and an oxyalkylene polymer having at least one silicon-containing group, which can be crosslinked through a siloxane of said group, wherein said silicon-containing group is represented by the formula II:

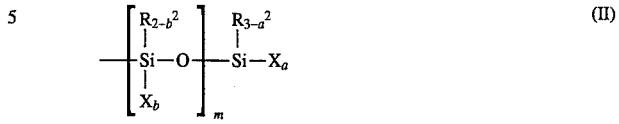

wherein X represents an hydroxyl group or hydrolyric group and when there are two or more X groups, the X groups may be the same or different; $R^2$ represents a monovalent hydrocarbon group having 1 to 20 carbon atoms or a triorganosiloxy group represented by $(R')_3SiO—$, wherein R' represents a monovalent hydrocarbon group having 1 to 20 carbon atoms and the three R' groups may be the same or different, and when there are two or more $R^2$ groups, the $R^2$ groups may be the same or different; a represents 0, 1, 2 or 3; b represents 0, 1 or 2; $1 \leq a+mb$, wherein m represents 0 or an integer of 1 to 19, and when m is 2 or more, the b numbers may not be identical, to human skin.

* * * * *